[19] United States Patent
Keutel

[11] 4,046,633
[45] Sept. 6, 1977

[54] DIRECT RENIN ASSAY SYSTEM AND METHOD

[75] Inventor: Hans J. Keutel, Salt Lake City, Utah

[73] Assignee: University of Utah, Salt Lake City, Utah

[21] Appl. No.: 484,472

[22] Filed: July 1, 1974

[51] Int. Cl.² ............................................. G01N 31/14
[52] U.S. Cl. ................................. 195/103.5 R; 195/99
[58] Field of Search ......................... 195/103.5 R, 99; 23/230 B

[56] References Cited

U.S. PATENT DOCUMENTS

| | | | |
|---|---|---|---|
| 3,607,859 | 9/1971 | Feder | 195/103.5 R |
| 3,788,948 | 1/1974 | Kagedal et al. | 195/103.5 R |
| 3,859,430 | 1/1975 | Parikh et al. | 195/103.5 R |

OTHER PUBLICATIONS

Bath et al., "Labeled Polymeric Substrate for Renin," Biochem., vol. 11, No. 15, (1972), pp. 2845-2853.
Ontjes et al., "Radiochemical Assay for Renin Utilizing a Synthetic Insoluble Substrate," Anal. Biochem. 45, (1972), pp. 374-386.

Primary Examiner—Raymond N. Jones
Assistant Examiner—C. A. Fan

[57] ABSTRACT

An assay system and method for the direct determination of the enzymatic activity of the enzyme renin in a biological sample. An enzyme specific octopeptide is incorporated into substrate which is immobilized at one end on an insoluble carrier and is tagged with a marker at the other. Through enzymatic activity, renin reacts with the substrate to cleave the octopeptide and thereby permit solubilization of the marker segment of the substrate. The solubilized marker can then be separated and quantified to indicate the amount of active renin in the sample.

12 Claims, No Drawings

DIRECT RENIN ASSAY SYSTEM AND METHOD

BACKGROUND

1. Field of the Invention

The present invention relates to the measurement of active renin enzyme in a biological sample.

2. The Prior Art

Hypertension is a clinical problem of major significance. It is estimated that approximately 23 million Americans have some form of hypertensive condition. Of these, approximately 15% are renal related, that is, dysfunction of the kidney is indicated and manifests itself in an increased renin level in the blood which is indicative of a renal related hypertensive condition. Of these persons having renal related hypertensive conditions a large number are susceptible to surgical correction after further examination has determined the exact cause for the renal involvement.

The production of renin is generally influenced by pathological changes in circulation (renovascular hypertension) and by mineral corticosteroid metabolism (hypertension related to adrenal gland diseases). Measurement of renin activity, therefore, appears to be of great importance for the identification of possible renal related hypertension. It has even been suggested that there is a striking correlation of coronary and cerebrovascular complications with increasing renin activity in essential hypertension.

Renin acts as a proteolytic enzyme of the kidney by releasing angiotensin which has a vasoconstrictive action which results in a higher blood pressure. The early detection of renin level increases related to a blood pressure increase will provide vital prognostic and diagnostic guidelines for evaluating possible surgical treatment especially in renovascular involvement.

There are presently available two types of renin enzyme activity measurement techniques: (1) bioassay, and (2) radioimmunoassay, both of which are based on indirect methods and are only reproducible under certain very controlled conditions and their reliability is accordingly, suspect.

The bioassay technique for measuring renin activity is based on angiotensin release after serum incubation. The isolated angiotensin from the incubated serum sample is injected into ganglion blocked rats and the resulting elevated blood pressure of the rat is compared with a standard curve which, in turn, is indicative of the renin level of the original sample.

The basic principle of radioimmunoassay utilizes the specific antigen-antibody reaction. This assay uses a known amount of antibody, present as a limiting factor, which is mixed with a sample containing the released Angiotensin I antigen, which is to be determined, and a known amount of radioactive or labeled antigen. The amount of labeled complex formed is an inverse factor of the Angiotensin I antigen concentration in the sample. The concentration of the antigen in an unknown sample is then determined by comparison with a standard curve.

Accordingly, it should be readily apparent that in each of the foregoing prior art techniques the methods are indirect methods and are considerably complex, time-consuming, difficult to standardize and of questionable reliability, particularly as between various research facilities using various different chemical products in their analysis. Accordingly, a rapid, sensitive, reliable, direct reading, and standardized assay technique for renin activity would be of great value in the diagnostic evaluation of hypertensive patients to determine those with possible renal involvement. The present invention offers such a technique for directly determining amount of active renin enzyme in a sample of either plasma or serum.

BRIEF SUMMARY AND OBJECTS OF THE INVENTION

The present invention takes advantage of the well-known characteristic of the enzymatic activity of renin for cleaving certain bonds between amino acids of an octopeptide, which is incorporated into a substrate. The technique includes immobilizing one end of the substrate on an insoluble carrier and attaching a marker to the free end of the immobilized substrate. Enzymatic activity of renin enzyme cleaves the bond between amino acids in the octopeptide, thereby liberating the market tagged segment of the substrate which can then be treated and assayed. The amount of marker assayed gives a direct indication of the enzymatic activity of the renin in the serum sample.

It is, therefore, a primary object of this invention to provide an assay system and method for determining the amount of active enzyme in a biological sample.

It is another object of this invention to provide an assay system and method for the direct determination of enzymatic activity of renin in a serum sample.

It is an even further object of this invention to provide a directly reading assay for enzymatic activity of renin wherein the marker may be a radioactive marker or a fluorescent marker.

These and other objects and features of the present invention will become more fully apparent from the following description taken in conjunction with the appended claims.

DETAILED DESCRIPTION OF THE PREFERRED EMBODIMENTS

General

To assist in the understanding of this invention, the following terms are employed and have the general meaning as indicated:

The substrate referred to herein may be indicated generally as follows:

(first extender)-(octopeptide)-(second extender).

The tagged substrate may be indicated generally as follows:

(first extender)-(octopeptide)-(second extender)-(marker).

The immobilized, tagged substrate may be indicated generally as follows:

(insoluble carrier)-(first extender)-(octopeptide)-(second extender)-(marker).

Each of these elements will be discussed more fully hereinafter.

In the presently preferred embodiment of this invention, the substrate has as its nucleus an octopeptide which is formed from the amino acids proline (hereinafter PRO); phenylalanine (hereinafter PHE), histidine (hereinafter HIS). leucine (hereinafter LEU), valine (hereinafter VAL), tyrosine (hereinafter TYR) and serine (hereinafter SER). These amino acids are formed into the octopeptide having a configuration of PRO-PHE-HIS-LEU-LEU-VAL-TYR-SER which is well-known to be enzyme specific for enzymaytic activity of renin enzyme in that enzymatic activity by active renin enzyme severs the LEU-LEU bond.

All future reference to an octopeptide hereinafter will refer to the octopeptide having the foregoing formulation. Other sequential arrangements of these amino acids exhibit a certain degree of specificity toward enzymatic action by renin; however, the present configuration is currently believed to be the most specific and sensitive for renin enzymatic activity.

It should be noted that the amino acid sequence within the octopeptide may be reversed without affecting the sensitivity of the substrate to the enzymatic action of renin. For ease of illustration, only one sequence, the left to right sequence, of the octopeptide is shown.

Advantage is taken of the specificity of active renin for the LEU-LEU bond of the octopeptide by suitably formulating a plurality of amino acids into a substrate with the octopeptide as the nucleus. The substrate is tagged with a marker at one end and is immobilized by being attached at the other end to an insoluble carrier. Renin acting upon the octopeptide in the immobilized, tagged substrate cleaves the LEU-LEU bond, and liberates the marker tagged segment of the substrate. The liberated marker tagged segment is then suitably treated and separated from the remaining marker and assayed to give a direct indication of the amount of active renin in the sample.

The Substrate

The preferred substrate usable with this invention is of the general formula:

(first extender)-(octopeptide)-(second extender)

The octopeptide used in this invention has previously been disclosed by others as the smallest combination of amino acids that exhibits specific activity for the enzymatic action of renin. Although naturally occurring in the blood, this octopeptide may be synthesized, for example, using the peptide synthesis technique known as the "Merrifield Technique" which is fully set forth in Solid Phase Peptide Synthesis by J. M. Stewart and J. D. Young, H. M. Freeman Company, San Francisco, California (1969).

The entire substrate and marker may also be synthesized using these conventional techniques; however, a number of commercial specialty chemical laboratories are able to prepare the substrate and marker of the presently preferred embodiments of this invention. One such firm, for example, is Bachem Fine Chemicals, Inc., Los Angeles, California.

The extenders are typically additional amino acid groups combined with the octopeptide to contribute the desired features of reliability and sensitivity as will now be more fully discussed.

Previous work has shown that there are unknown factors involved in the different reactions of an enzyme with an insoluble substrate versus a soluble but immobilized substrate. Accordingly, a soluble substrate is used and is only immobilized on an insoluble carrier. However, the presence of an insoluble carrier adjacent the octopeptide has been found to hinder the enzymatic severance of the LEU-LEU bond by renin. To minimize this interference by the carrier, additional amino acids, as a first extender, are included as part of the substrate between the octopeptide and the insoluble carrier so as to extend the LEU-LEU bond farther from the carrier.

Interference with the enzymatic action of active renin enzyme on the LEU-LEU bond of the octopeptide may also be created by the marker with which the substrate has been tagged. To reduce this interference, additional amino acid groups may also be interposed between the octopeptide and the marker as a second extender, the number of amino acid groups being selected to correspond to the characteristics of the marker used for tagging the substrate.

Accordingly, the immobilized, tagged substrate has the following general formula:

(insoluble carrier)-(first extender)-(octopeptide)-(second extender)-(marker).

In the presently preferred embodiments of this invention, both extenders are composed of glycine amino acid groups (hereinafter GLY) with the total number of GLY in each extender being determined by the need for providing desired separation between the LEU-LEU bond of the octopeptide and the source of possible interference. For example, if commercially available biological support glass beads are used for the carrier, as will be more fully discussed hereinafter, three GLY groups have been found desirable as the first extender. Greater or lesser GLY groups may be used depending upon the interference considerations. Clearly, other suitable extender groups besides GLY may be used as long as the extender groups serve in the function of separating the LEU-LEU bond of the octopeptide from the source of interference.

The foregoing discussion is equally applicable to the second extender. For example, in the presently preferred embodiments of the present invention, GLY groups are also used in the second extender with one GLY group being used for a fluorescent marker whereas four GLY groups are used when an isotope of iodine is used as a radioactive marker. GLY is presently preferred for the role of forming the first and second extenders because the GLY-GLY bond is less susceptible to carboxypeptidasis or cleavage by enzymatic activity.

The foregoing general formula may, therefore, be more specifically indicated as:

(Insoluble Carrier)-GLY-GLY-GLY-PRO-PHE-HIS-LEU-LEU-VAL-TYR-SER-GLY-(Fluorescent Marker)-VAL.

VAL appears on the end of the tagged substrate since the VAL formed the starting resin for the synthesis of the tagged substrate. Any other suitable starting material could also be used in this synthesis.

When the octopeptide is split at the LEU-LEU bond, the marker tagged segment is liberated leaving the remainder of the substrate immobilized on the carrier. The liberated segment has the following general formula:

(split octopeptide, tetra peptide)-(second extender)-(marker).

An analysis of the amino acids in the substrate was obtained after an acid hydrolysis for 20 hours at 103° C with constant-boiling-point hydrochloric acid. The amino acid analysis gave the following quantitative data for the substrate, the theoretical values being stated parenthetically:

HIS 0.93 (1), SER 0.906 (1), PRO 0.73 (1), GLY 4.0 (4), VAL 1.89 (2), LEU 2.1 (2), PHE 1.18 (1).

It should be noted that the TYR was also a constituent of the fluorescent marker and was difficult to measure since most of it precipitated in the buffer used for the analysis.

The Marker

The marker is chosen so as to give an outward manifestation of its presence which can be measured to ascertain the quantity of marker present, the quantity being indicative of the active renin enzyme in the sample. Colorimetric, fluorescent, or radioactive markers may be used.

In the presently preferred embodiments of this invention, both fluorescent and radioactive markers have been used to tag the substrate. One fluorescent marker found suitable for tagging is a TYR amino acid which has been combined with a fluorescent dye wherein attachment has taken place at the OH side group of the TYR.

The fluorescence is provided by a fluorescent dye, 1-dimethylaminonaphthalene-5-sulfochloride, which is attached as the marker to the TYR which attachment procedure is referred to by G. Weber in Biochemistry Journal, Vol. 51, at pages 155–167 (1952) as dansylation and is therefore referred to hereinafter as Dans. Accordingly, the term (O-Dans-TYR) is a short hand expression for the foregoing dansylated TYR and will be used hereinafter to indicate the same. Obviously any other suitable fluorescent dye could be used for this procedure. The fluorescent marker, (O-Dans-TYR), is commercially available from Bachem Fine Chemicals, Inc., Los Angeles, California.

To provide a sufficient degree of sensitivity to the system, several (O-Dans-TYR) marker groups are attached as the marker to the second extender of the substrate. In the presently preferred embodiment of this invention, 15 (O-Dans-TYR) marker groups are used. Although as low as six (O-Dans-TYR) marker groups have been successfully used, this small number was less sensitive and was deemed less desirable. Practically any number of marker groups could be used so long as they did not interfere with the renin specific severance of the LEU-LEU bond and provide sufficient sensitivity.

Using the solid phase peptide synthesis described by Merrifield, as previously set forth, 28 amino acids (including fifteen TYR in the (O-Dans-TYR) fluorescent marker) were coupled together to provide the tagged substrate herein. The tagged substrate had the following formula:

GLY-GLY-GLY-PRO-PHE-HIS-LEU-LEU-VAL-TYR-SER-GLY-(O-Dans-TYR)$_{13}$-VAL and had a molecular weight of 7757.

One radioactive marker group found useful in the presently preferred embodiment of the present invention is a radioactive isotope of iodine, I(125). The I(125) is attached to a TYR molecule so that the marker is I(125)-TYR. Iodine has an approximate molecular size equal to the combined size of about four amino acid molecules. Therefore, to prevent the iodine marker molecule from interfering with the enzymatic cleavage by renin of the LEU-LEU bond, at least four additional amino acid groups (GLY in this presently preferred embodiment) are placed in the molecular chain of the substrate between the octopeptide and the I(125) marker as the second extender.

Following essentially the same synthesis technique as for preparation of the fluorescent marker tagged substrate, a radioactive marker tagged substrate may also be prepared and have the following configuration:

GLY-GLY-GLY-PRO-PHE-HIS-LEU-LEU-VAL-TYR-SER-GLY-GLY-GLY-GLY-I(125)-TYR-VAL.

Tagging the substrate with a radioactive isotope of iodine, I(125), to create the tagged substrate of this invention may present certain problems relating to (1) the relatively short half life of I(125) which is only about 60 days and (2) instability of the substrate upon labeling I(125). These problems may be effectively overcome by separately labeling a smaller polypeptide, for example, a pentapeptide, and later coupling the pentapeptide as the marker to the remaining portion of the substrate. By this technique, it is possible to provide fresh I(125) marker and simultaneously minimize the destruction of the substrate by the labeling procedure.

This technique involves preparing the substrate according to the previously set forth techniques followed by immobilization by attachment to the insoluble carrier. This segment of the substrate has no marker and may be referred to as the immobilized substrate and has the general formulation:

(Insoluble Carrier)-(First Extender)-(Octopeptide)-(Second Extender)

The carboxylic group on the last amino acid of the second extender may then be converted to an activated group such as an acetyl chloride or, preferably, an ester, for example, by reaction with n-hydroxy-succinimide. Further reaction of the ester with ethylenediamine furnishes an amine group, (NH$_2$), on the end of the chain to form:

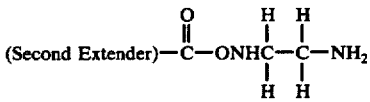

The NH$_2$ then serves as the active site for creating a peptide bond between the substrate and the marker.

The marker is also formulated according to the previously discussed peptide synthesis techniques and includes the isotopically labelled TYR, I(125)-TYR. Such a labeling technique may be found in a literature reference, "The Labelling of Proteins to High Specific Radioactivities by Conjugation to a I(125)-containing Acylating Agent" by A. E. Bolton and W. M. Hunter, Biochem. J., Vol. 133, pp 529–539 (1973).

After the pentapeptide has been labelled to create the marker, an active site on one end of the marker is prepared for reaction with the active site on the substrate so as to create a peptide bond between the marker and substrate upon reaction.

The marker may also be further modified by the inclusion of a fluorescent marker group, (O-Dans-TYR), so as to provide a technique for standardizing the radioactive iodine labelled marker. For example, the structure may be designated as follows:

(O-Dans-TYR)-GLY-I(125)TYR-VAL.

The reason for the inclusion of the fluorescent labelled marker group in the marker will now be discussed.

Since isotopic materials require and are thus prepared in minute quantities, it is extremely difficult to determine the degree to which the marker has been isotopically labelled per unit weight of marker. For this reason it is proposed that the isotopically labelled amino acid marker be incorporated into a pentapeptide which includes a fluorescent marker group, for example, (O-Dans-TYR). With the double labelling of the pentapeptide, it is possible to measure both the fluorescence and the radioactivity as a technique for determining the ratio of I(125) per unit weight of material and thus it is a simple procedure to pepare a standard curve according to conventional biochemical techniques.

This method of standardization is preferred since not all isolated renin exhibits the same degree of enzymatic activity, thus making it difficult to use isolated renin for preparing a standard curve.

The pentapeptide marker has a structure that includes an n-acetylated alanine (hereinafter ALA) which is chosen because of its availability and low number of possible activation sites. The marker may be chemically designated as follows:

n-acetylated ALA-(O-Dans-TYR)-GLY-I(125)-TYR-VAL.

The VAL is then esterfied and the ester serves as the attachment site for coupling the pentapeptide marker to the active site on the substrate.

The Insoluble Carrier

The insoluble carrier used in the presently preferred embodiments of this invention are glass beads specifically designed as a biological support material and are commercially available from Corning Glass Works, Inc., Corning, New York, and are designated as Corning Biological Support Material (GAO-3940) 80–120 mesh. As available, the glass beads may be chemically designated as follows:

(Glass Bead)—$NH_2$.

The glass beads, with the 0.14 meq/g amino groups, are reacted with succinic anhydride followed by esterification with n-hydroxy-succinimide according to conventional chemical techinques and the resulting product may be chemically designated as follows;

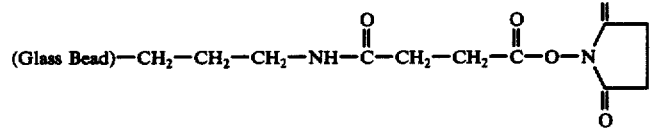

all of which is herein referred to as the insoluble carrier.

Activation of the glass beads with the amino groups provides the attachment site for the first extender group by replacement of the ester with the first GLY of the first extender group.

With the attachment of the tagged substrate to the insoluble carrier, the tagged substrate is immobilized and suitable for use in a renin assay system.

The estimated quantity ot tagged substrate coupled to one gram of glass beads ranged from 20 to 25 micrograms thereby avoiding an overload of the glass beads which overload would interfere in the interaction of the active renin enzyme with the octopeptide nucleus of the tagged, immobilized substrate.

Although biomaterial support glass beads have been used as the insoluble carrier for this invention, other suitable insoluble carrier material may be used including, for example, cellulose, nylon, and resins.

Assay for Renin Activity in Serum

Under proper conditions, enzymatic activity of active enzyme renin will hydrolyze the octopeptide within the foregoing tagged, immobilized substrate and liberate the marker segment portion thereof. The liberated marker tagged segment is then separated from the unreacted, immobilized substrate by solubilization and separation by mechanical means, for example, centrifugation. The fluorescence or radioactivity of the separated, marker-tagged segment is measured and compared with a standard curve to evaluate the relative amount of active renin enzyme in the sample.

A serum or plasma sample from which the blood cells have been separated contains a certain quantity of a natural polypeptide which has therein an octopeptide substantially identical to that of the substrate. Although it is possible to achieve suitable results by assaying a serum sample containing this natural octopeptide, it is preferable to destroy this natural octopeptide in the serum before proceeding with the assay.

To more clearly set forth the effect of the destruction of this natural octopeptide in the blood sample as compared with leaving the natural octopeptide unchanged, the following data of Table I was obtained through an experimental procedure. In Table I, the natural octopeptide in several samples was destroyed and the enzymatic activity of renin was measured with the results set forth in column (A) as nanograms/milliliter/hour (ng/ml/hr). The same information for similar samples was obtained in samples wherein the natural octopeptide remained unchanged. A significant increase in the indicated enzymatic activity of renin within the plasma was found by comparing the respective columns of the two test groups.

Destruction or inactivation of the naturally occurring octopeptide is accomplished by hydrolysis of the serum sample with acid at a pH of 3.0 while holding the sample at 30° C for 1 hour.

TABLE I

RENIN ACTIVITY IN HUMAN PLASMA

| (A) Natural Octopeptide | (B) Natural Octopeptide |
| --- | --- |
| Inactivated | Unchanged |
| ng/ml/hr | ng/ml/hr |
| 18.8 | 2.4 |
| 26.5 | 4.42 |
| 47.1 | 12.1 |
| 67.7 | 13.6 |
| 97.2 | 26.6 |
| 140.3 | 37.1 |
| 155.6 | 45.0 |

To proceed with the assay, the pH of the serum sample is readjusted to 5.5 with 0.1 N NaOH after which a known quantity of the immobilized, tagged substrate is mixed with the sample and deaerated under the partial vacuum in a dessicator for about 5 minutes after which it is incubated in a 37° C water bath for 1 to 3 hours.

During incubation the enzymatic activity of active renin enzyme cleaves the LEU-LEU bond of the octopeptide and liberates the marker tagged segment of the substrate which forms a precipitate at that pH.

It has been found that at the pH values used in this assay technique that the fluorescent marker tagged segment is insoluble upon liberation and forms a precipitate. This is convenient in that it permits washing of the precipitate to remove contaminating background fluorescence and protein which tends to interfere with the assay. The precipitate is washed with saline buffered to pH 7.0.

On the other hand, radioactive marker tagged segments do not require washing and may be solubilized and assayed immediately.

After washing, the marker tagged segment precipitate is dried under partial vacuum at room temperature. The marker tagged segment is then dissolved in a 1:1 mixture of dimethylformamide and dioxane at pH 7.0. (This particular pH is chosen since the silica complex of the glass beads tends to be unstable at higher pH values.) After incubation for 10 minutes followed by centrifugation, the supernate is decanted and the marker therein measured with a suitable device, e.g. a scintillation counter or fluorometer according to conventional techniques.

An isotopically tagged substrate may be preferred over a fluorescent tagged substrate since many hospitals, laboratories, etc. have existing equipment for measuring radioactivity and the radioactive marker segment does not require washing before being measured as does the fluorescent marker.

The invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A substrate having a specificity for the enzymatic action of renin enzyme comprising:
   an octopeptide having the general formulation: PRO-PHE-HIS-LEU-LEU-VAL-TYR-SER;
   a marker attached at one end of the substrate;
   an insoluble carrier attached at the other end of the substrate so as to immobilize the substrate and attached marker.

2. A substrate as defined in claim 1 wherein the marker is attached to the substrate with at least one GLY amino acid.

3. A substrate as defined in claim 1 wherein the marker comprises a fluorescent marker.

4. A substrate as defined in claim 3 wherein the fluorescent marker is an amino acid which has a fluorescent dye attached at a hydroxyl side group of the amino acid.

5. A substrate as defined in claim 4 wherein the fluorescent dye is 1-dimethylaminonapthalene-5-sulfochloride.

6. A substrate as defined in claim 1 wherein the marker is a radioactive isotope.

7. A substrate as defined in claim 6 wherein the marker is attached to an amino acid.

8. A substrate as defined in claim 6 wherein the radioactive isotope is I(125).

9. A substrate as defined in claim 1 wherein the insoluble carrier is selected from the group consisting of glass bead, cellulose, resin, and nylon.

10. An immobilized substrate having specificity for enzymatic action by active renin enzyme comprising:
    an insoluble carrier;
    a first extender attached to the carrier;
    an octopeptide comprising an amino acid chain in the sequence of PRO-PHE-HIS-LEU-LEU-VAL-TYR-SER, the octopeptide being attached at a first end to the first extender;
    a second extender attached to a second end of the octopeptide;
    a marker attached to the second extender.

11. A method of providing a system for the assay of enzymatic activity of renin comprising the steps of:
    obtaining an octopeptide having a formulation of amino acids in a sequence of PRO-PHE-HIS-LEU-LEU-VAL-TYR-SER;
    incorporating the octopeptide into a polypeptide so as to form a substrate;
    immobilizing the substrate by attaching one end to an insoluble carrier;
    reacting the other end of the substrate with a material which enhances the coupling of an amino acid with the substrate, thereby preparing an activated end of the substrate; and
    coupling a radioactive isotope labelled amino acid to the activated end of the substrate.

12. A method for assaying enzymatic activity of active renin enzyme in a biological sample comprising the steps of:
    obtaining an octopeptide having a formulation of amino acids in a sequence of PRO-PHE-HIS-LEU-LEU-VAL-TYR-SER;
    incorporating the octopeptide in a soluble polypeptide substrate;
    tagging the substrate by attaching a marker at one end;
    immobilizing the tagged substrate by attaching the other end of the substrate to an insoluble carrier;
    contacting the immobilized, tagged substrate with a biological sample so as to permit enzymatic activity of active renin enzyme in the sample to sever the LEU-LEU bond of the octopeptide thereby liberating the marker tagged segment of the substrate;
    solubilizing the marker tagged segment of the substrate;
    separating the solubilized marker tagged segment of the substrate from the remaining immobilized substrate; and
    measuring the marker in the separated portion.

* * * * *